United States Patent [19]
Berthold et al.

[11] Patent Number: 5,206,711
[45] Date of Patent: Apr. 27, 1993

[54] FLUID OPACITY SENSOR

[75] Inventors: John W. Berthold, Salem; Charles R. Dailey, Akron, both of Ohio

[73] Assignee: The Babcock & Wilcox Company, New Orleans, La.

[21] Appl. No.: 535,934

[22] Filed: Jun. 11, 1990

[51] Int. Cl.⁵ ............................................. G01N 21/00
[52] U.S. Cl. ..................... 356/436; 356/435; 356/440
[58] Field of Search ................. 356/432–436, 356/440–441, 410–411; 250/573–576, 227.11, 227.14

[56] References Cited

U.S. PATENT DOCUMENTS

| | | | |
|---|---|---|---|
| 3,972,625 | 8/1976 | Takahasi et al. | 356/435 |
| 4,637,729 | 1/1987 | Schoch | 356/436 |
| 4,851,665 | 7/1989 | Presavento et al. | 356/436 |
| 4,860,586 | 8/1989 | Miers et al. | 250/227.16 |
| 4,917,491 | 4/1990 | Ring et al. | 356/440 |
| 4,989,942 | 2/1991 | Koenigsberg et al. | 356/436 |

Primary Examiner—F. L. Evans
Assistant Examiner—K. P. Hantis
Attorney, Agent, or Firm—Vytas R. Matas; Robert J. Edwards; Daniel S. Kalka

[57] ABSTRACT

A fiber optic fluid opacity sensor includes a light source (12) transmitting light to dividing means (14) for providing a sample light signal (18) and a reference light signal (20) to dual photodetectors (26, 28). Sample and reference optical pathways (19, 21) are defined by optical fibers (18, 20) spaced apart from and axially aligned with the photodetectors (26, 28) at a predetermined distance. Signal processing means (30) takes the log ratio output of the signals from the photodetectors (26, 28) for cancelling the effect of light source drift since the same source (12) is common to both for measuring the light transmission and determining opacity therefrom. A sample probe (40) contains the photodetectors (26, 28) and the sample and reference optical pathways (19, 21). The light source (12) and the signal processing means (30) are situated outside of the probe (40) and by virtue thereof outside of the sample process line (48).

18 Claims, 5 Drawing Sheets

Flow Direction

FLUID OPACITY SENSOR

BACKGROUND OF THE INVENTION

1. Field of the Invention

The present invention relates in general to a fluid opacity sensor, and, in particular, is directed to a fiber optic fluid opacity sensor for measuring opacity of a fluid in a process line.

2. Description of the Related Art

Opacity monitors are known for measuring how much light is blocked by gases passing through a conduit or stack as taught in U.S. Pat. Nos. 4,583,859 and 4,381,153. This measurement of opacity for the gases is a measurement of the amount of particles or smoke in the gas.

Paint is composed of several major ingredients including titanium dioxide ($TiO_2$), acrylic latex, and water. At various stages in paint processing, the relative concentration of $TiO_2$ must be measured to support process control. $TiO_2$ is optically very dense and its concentration in mixtures with water and latex can be determined by the measurement of the opacity of the mixture.

Opacity may be defined as the inverse of transparency, or $$O = I_o/I_{tr} \tag{1}$$

where:

O = Opacity,
$I_o$ = Incident intensity, and
$I_{tr}$ = Transmitted intensity

Early attempts to measure paint opacity in a process line used a single light source and detector inserted in a probe. This probe was inserted into a process line. The measurement of light transmission through a small gap where the paint was permitted to flow provided a measure of paint opacity or optical density. Difficulties with a single source/single detector approach included thermal drift of the detector, intensity variation of the source, and 60 Hz line noise pick-up in the processing electronics. All of these problems resulted in poor repeatability and large errors in measured opacity over extended periods of time.

Because of the foregoing problems associated with the prior art devices, it has become desirable to develop a fluid opacity sensor with an adequate signal-to-noise ratio while maximizing the optical path length so as to avoid clogging the sensor with fluid deposits. The term fluid as used herein is meant to include both gases and liquids. The fluid opacity sensor should provide compensation for light source variations as well as compensating for temperature drift. The fluid opacity sensor should also allow for periodic calibration with a minimum of effort and for the measurement of transmitted light intensity over a wide dynamic range.

SUMMARY OF THE INVENTION

The present invention solves the foregoing problems associated with the prior art as well as other problems by providing a fiber optic fluid opacity sensor. The fiber optic fluid opacity sensor includes a light source which transmits light to a light divider means. The light divider means splits the light signal into a sample signal and a reference signal. The sample signal and the reference signal are transmitted via optic fibers into a sample probe which is inserted in a process line. In the sample probe, there are defined two optical pathways, a sample optical pathway and a reference optical pathway, with both optical pathways being defined by optical fibers spaced-apart from and axially aligned with photodetectors at a predetermined distance. The sample optical pathway is provided with windows, which allows the sample fluid to pass between for measuring opacity. The optical pathway passes through the windows, but the sample fluid pathway passes between the windows. The reference optical pathway is sealed from sample ingress. The light signal from the same light source propagates through both optical pathways. A signal processing means in communication with the photodetectors takes a log ratio of the output currents to cancel the effect of light source drift since the same light source is common to both optical pathways. The effects of thermal drift and 60 Hz noise are cancelled to the extent that they are identical in each optical pathway, as taught in U.S. Pat. No. 4,860,586.

An aspect of the present invention is to provide a real-time, in-process fluid opacity sensor.

Another aspect of the present invention is to provide a fiber optic fluid opacity sensor which is repeatable and easily maintainable.

A further aspect of the present invention is for the sensor to exhibit a wide measurement range thus permitting a variety of opacity ranges to be measured with a single device.

A still further aspect of the present invention is to provide a fiber optic fluid opacity sensor which compensates for light source variations and thermal drift.

The various features of novelty characterized in the present invention are pointed out with particularity in the claims annexed to and forming a part of this disclosure. For a better understanding of the invention, and the operating advantages, attained by its use, reference is made to the accompanying drawings and descriptive matter in which the preferred embodiment of the invention is illustrated.

DESCRIPTION OF THE PREFERRED EMBODIMENT

Figure 1:
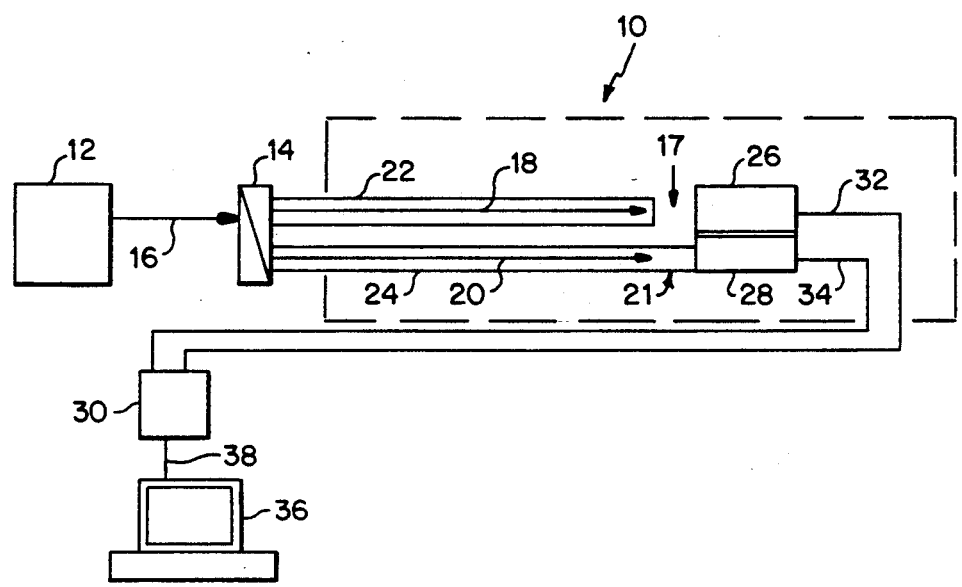
FIG. 1 is a schematic representation of the present invention.

Referring now to the drawings where the illustrations are for the purpose of describing the preferred embodiment of the present invention and are not intended to limit the invention hereto, FIG. 1 is a schematic representation of the fiber optic fluid opacity sensor of the present invention. Only the portion (10) shown in dashed line is introduced to a sample stream (not shown). The fiber optic fluid opacity sensor includes a light source (12) such as a laser diode, light-emitting diode (LED) or incandescent source which transmits light to a light divider means (14). The light preferably is transmitted via an optical fiber (16). Light divider means (14) includes an optical fiber coupler or some other form of beam splitter to divide the transmitted light into a sample signal and a reference signal. The sample and reference signals are transmitted by way of optical fibers (18, 20) respectively.

The optical fibers (18, 20) are positioned in channels or conduits (22, 24), respectively. A sample optical pathway (19) is defined by optical fiber (18) being spaced apart from and axially aligned with photodetector (26) at a predetermined distance. A reference optical pathway (21) is defined by optical fiber (20) being spaced apart from and axially aligned with photodetector (28) at a distance approximately equal to that employed in the sample optical pathway (19). Both photodetectors (26, 28) provide output currents to signal processing means (30) along lines (32, 34).

A computer or microprocessor (36) may be provided in communication with signal processing means (30) by line (38) for displaying the measured values and/or further processing the signals therefrom.

Figure 2:
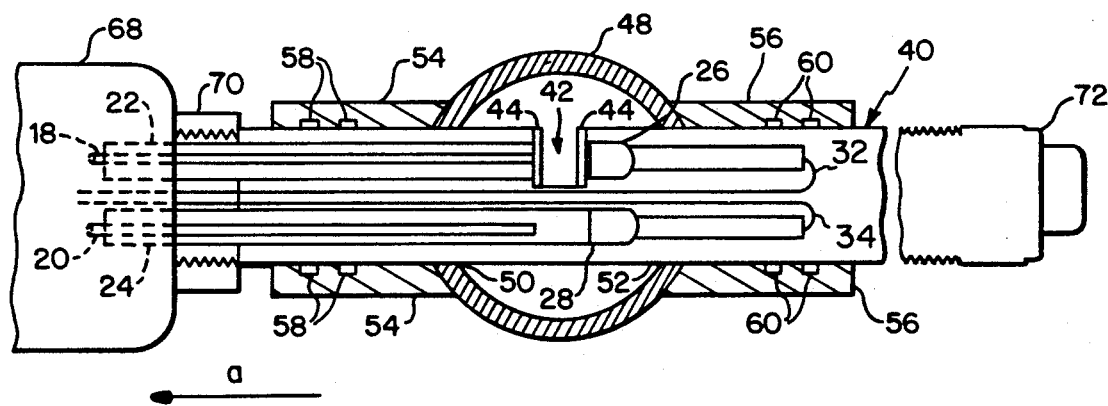
FIG. 2 is a cross-sectional illustration of a portion of the preferred embodiment of the present invention in a sample process line.

In the preferred embodiment of the present invention, the fiber optic fluid opacity sensor comprises a sample probe (40) as illustrated in FIG. 2. Sample probe (40) includes optical fibers (18, 20) positioned in channels (22, 24) being spaced-apart from and axially aligned with photodetectors (26, 28) at a predetermined distance. Preferably, for paint this distance is about 1.6 mm. For other fluids, this distance may vary.

An optical pathway (19), as shown in FIG. 1, traverses a passage (42), shown in FIG. 2. Passage (42) allows sample to pass therethrough for measuring opacity. Windows (44) are provided to protect the distal end of optical fiber (18) and photodetector (26). Suitable windows (44) include lenses or filters well known in this art.

Figure 5:
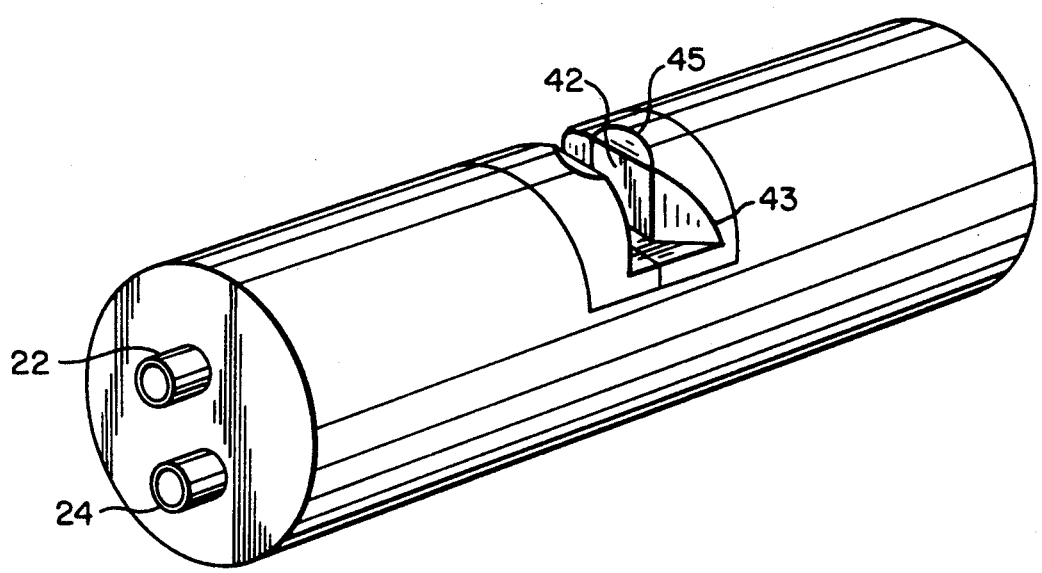
FIG. 5 is a perspective view of the preferred sample pathway.
Figure 6:
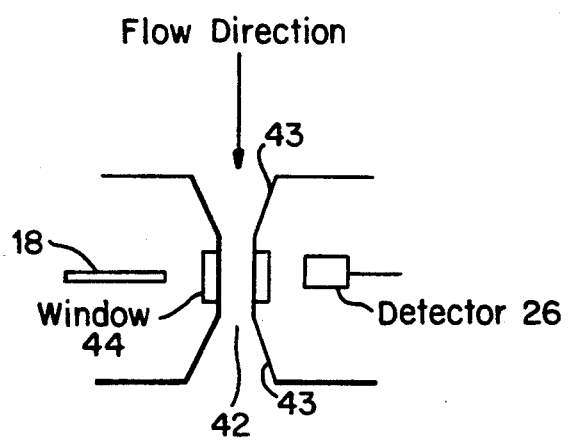
FIG. 6 is a top plan view of FIG. 5.

The reference optical pathway (21) is sealed from sample ingress, but is situated proximate the sample optical pathway (19) for exposure to a similar environment. In the preferred embodiment, the sample pathway (42) shown in FIG. 5 is rectangular to accommodate easy mounting of the windows, for access to the optical pathway and to maintain a fixed width for the sample path. When the probe is to be used with viscous fluids, the sample pathway outboard (43, 45) of the windows is flared as shown in FIGS. 5 and 6. With this configuration, the pressure drop is reduced for fluid traversing the sample path (42).

Light source (12) dividing means (14), and signal processing means (30) in FIG. 1 are located outside of sample probe (40) as depicted in FIG. 2. The output currents from photodetectors (26, 28) are sent to the signal processing means (30) through lines (32, 34) which extend axially through sample probe (40) in channel (46) as best seen in FIG. 3.

FIG. 2 depicts sample probe (40) extending through a sample process line (48). While it is preferred that the sample probe (40) pass completely through the sample process line (48) through apertures (50, 52). It is only important that the sample and reference optical pathways (19, 21) of the sample probe (40) be located to provide representative measurements. Of course, probe (40) may be situated in a process tank (not shown), or a diverted sample line.

Sample process line (48) has nozzles (54, 56) attached thereto with nozzles (54, 56) being in substantial axial alignment with apertures (50, 52). Nozzles (54, 56) are attached to sample process line (48) by welding or any suitable manner, and are adapted to receive sample probe (40) in a close fitting relationship. The nozzles (54, 56) have sealing means (58, 60) which preferably are resilient O-rings, but other suitable sealing materials such as packing glands may be used. Sealing means (58, 60) prevents sample from escaping out of the sample process line (48). The sample flows in sample process line (48) in a direction perpendicular to the plane of the paper. In addition, sealing means (58, 60) allows the sample probe (40) to be partially withdrawn from the sample process line (48) in the direction of arrow (a) for cleaning passage (42) and setting the offset adjustment without interruption of the manufacturing process. The sample probe (40) is of sufficient length that the distal end of probe (40), that is, the end with cap (72), is still in contact with sealing means (60). However, passage (42) is located out of sample process line (48) and nozzle (54) where it is available for maintenance.

Figure 3:
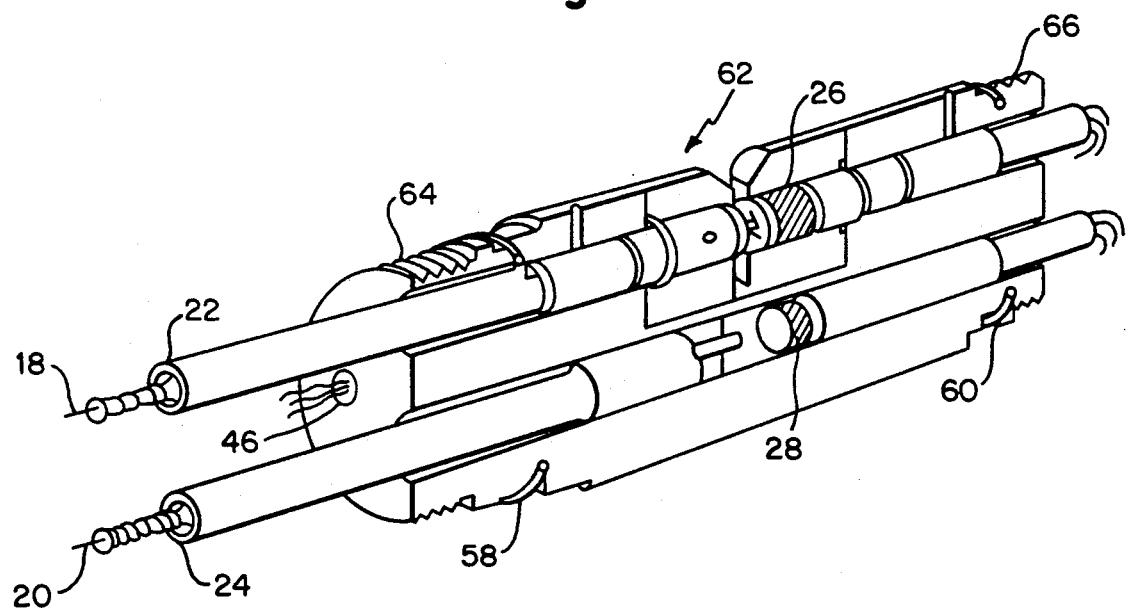
FIG. 3 is a cross-sectional illustration of a portion of the preferred embodiment of the present invention.

FIG. 3 depicts a cross-section of the main body (62) of the sample probe (40). The main body (62) has threads (64, 66) at both ends to enable easy assembly at a process site. The preferred embodiment has extension tubes which effectively lengthen the body to permit on-line maintenance. The sample optical passageway (19) is shaped to route a representative fluid sample into the optical path of the sensor while limiting the accumulation of deposits on the windows (44). Also, the single-ended probe design allows the sample region of the probe to be withdrawn from the process line (48) without compromising the fluid/pressure boundary. This design feature permits cleaning and offset adjustment without interrupting the manufacturing process.

A container (68), in FIG. 2, used for holding the signal processing means (30) is mounted on a threaded flange (70) for receiving the threaded body (62) of sample probe (40). In a similar fashion, cap (72) is threaded for receiving the threads (66). This modular design facilitates assembly and transportation.

Figure 4:
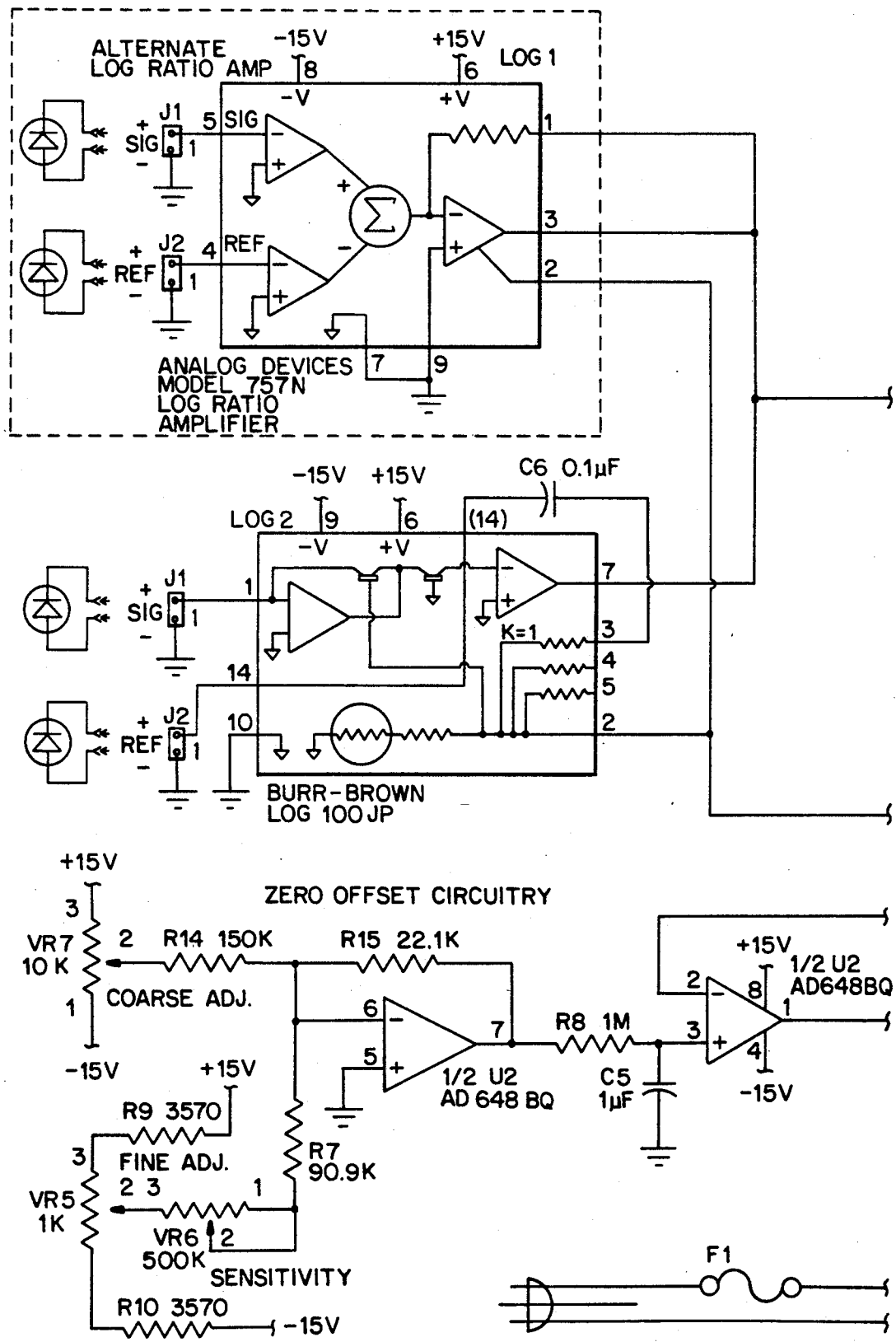
FIG. 4 is a schematic diagram of the signal processing electronics for the preferred embodiment of the present invention.
Figure 4:
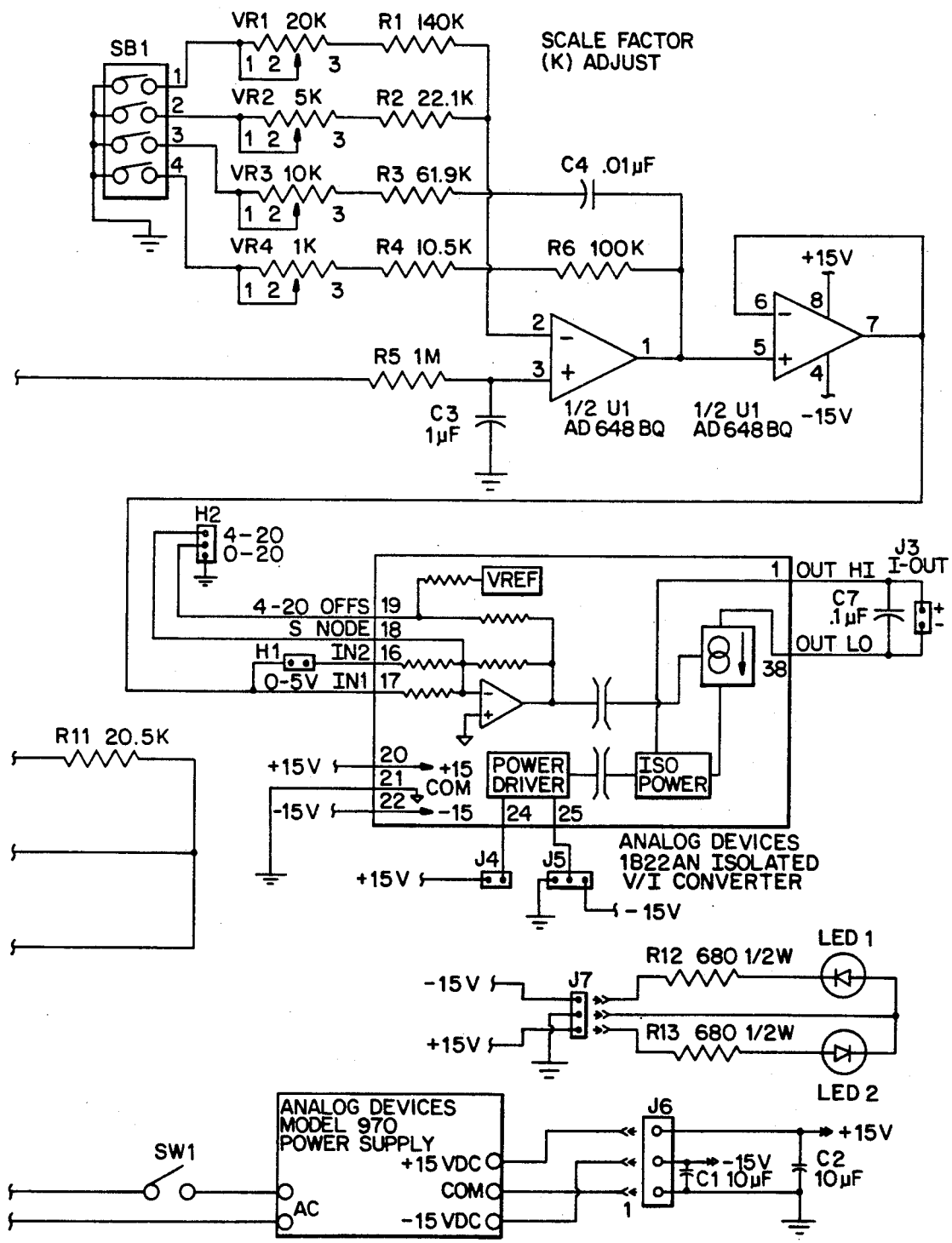

FIG. 4 is a schematic diagram of the signal processing means (30) used in the present invention.

The fiber optic fluid opacity sensor of the present invention finds particular utility as an opacity probe for paint, but it is useful for monitoring opacity of any liquid or gas. The sensor is intended to be employed in a sample process line (48) through which mixtures of water, acrylic latex, and titanium dioxide ($TiO_2$) flow, as is well known in this art.

The opacity, as measured by the present invention, is defined in units derived from the following equation:

$$Opacity = Log\ I_{ref}/I_{sig} - Offset \qquad (2)$$

where $I_{ref}$ and $I_{sig}$ are the photocurrents generated by incident light falling upon the photodetectors (26, 28).

When air is in the sample optical pathway (19), $I_{ref}$ and $I_{sig}$ are substantially equal and so the first term of equation (2) is approximately zero. An arbitrary offset is subtracted by means of a trimpot adjustment as schematically shown in FIG. 4 to bring the net result to exactly zero. This effectively sets the opacity unit of air to zero.

When an opaque sample is introduced into the sample optical pathway (19), $I_{sig}$ will drop by some value proportional to the opacity of the sample. If $I_{sig}$ falls by one order of magnitude, the net result of this equation is the value of one. Therefore, the opacity unit is defined as the difference in orders of magnitude of change in generated photocurrent between air (or some other calibration fluid) and an opaque sample at a predetermined pathway of about 1.6 mm. The fiber optic fluid opacity sensor is capable of measuring opacity over a range of six units referenced to air. Laboratory experimentation has shown that the opacity of titanium dioxide/latex mixtures falls in the 2-6 unit range while the opacity of latex/water mixtures falls in the 2-3 unit range.

The signal output from the sensor is 4-20 mA. The span range of the sensor is switch selectable with embodiment depicted having four switches. This output can represent either 1, 2, 4 or 6 opacity units of span, and 0-4 units of offset. Of course, more switches may be added to the circuit shown in FIG. 4 for a complete span range.

The sensor operating range is selectable by setting dip switches in the signal processing means. A gross adjustment of "zero offset" is made with sensitivity pot (VR7) in FIG. 4. A fine adjustment of "zero offset" is made with sensitivity pot (VR6).

The sensor is initially set to the six decade range and zeroed with air as a reference opacity (i.e., in air the probe output is 4 mA and when light transmission is reduced by six orders of magnitude, the probe output is 20 mA).

Neutral density filters (not shown) with nominal values of 1, 2, 3 and 4 which represent 1-4 orders of magnitude reduction in light transmission may be used to verify proper sensor operation. The neutral density filters serve a dual purpose: first, they are useful as a calibration check, and second, as a standard for adjusting the zero offset. Neutral density filter values are wavelength dependent and if the light being used in the opacity meter is broad band, the neutral density filter value may not correspond exactly to the change in light transmission. The filters do, however, provide a repeatable opacity for checking proper operation of the sensor.

The proper operation of the sensor may be checked by inserting various neutral density filters in the sample optical pathway (19), covering it with a black cloth, and comparing the measured output to previously obtained values. The probe output should be reproducible at each neutral density value.

A neutral density filter with a nominal value may not reduce the light transmission emanating from the broadband source used by the sensor by the nominal value. It does however reduce the light transmission by the same amount each time it is used.

The fluid opacity sensor of the present invention provides the following advantages over the prior art devices. First, by employing fiber optics to transmit light to the sample optical pathway (19), there is increased optical power compared to direct light input which is limited by the adverse impact of bulb heat generation on optical detectors and other sensor components. The increase in available optical power permits a measurable opacity range corresponding to six decades of transmitted light intensity.

Second, the fluid opacity sensor according to the present invention is configurable for spans of 1, 2, 4 or 6 opacity units corresponding to the 1, 2, 4 or 6 decades of transmitted intensity by adjusting dip switch (SB1) settings and 0-4 opacity units of offset by adjusting variable resistors (VR5, VR6, VR7). This allows the same sensor to be used at many different processing points with widely variant nominal opacities.

Third, the sensor requires only zero adjustment or standardization to verify calibration. A value of zero opacity is assigned to air which allows the sensor calibration to be verified simply by purging the sample optical pathway (19) of fluid.

Fourth, adjustable zero offset (standardization) permits compensation for changes in the light transmission due to all envisioned error sources which include deposits or abrasion of optical windows (44) without affecting sensor calibration or sensitivity.

Fifth, opacity sensor optics and signal processing are designed to be self-referencing with respect to variations in light source intensity, ambient temperature, and condition of cables and connectors.

Finally, the mechanical design of the present invention simplifies sensor maintenance.

Certain modifications and improvements will occur to those skilled in the art upon reading the foregoing description. It is understood that all such improvements and modifications have been deleted herein for the sake of conciseness and readability but are properly within the scope of the following claims.

An example of such a modification is to employ either a bifurcated fiber optic cable, or two separate fiber optic cables for the sample and reference optical fibers.

Another example is to supply purging air for cleaning windows (44), and to replace 4-20 mA lines and computer processing with a self-contained LED readout that displays actual opacity units.

We claim:

1. A fiber optic fluid opacity sensor for measuring opacity of a sample, comprising:

a light source;

means for dividing light from said light source into a sample signal and a reference signal;

a sample optical pathway for transmitting said sample signal through a sample in a passage defined by a predetermined distance;

a reference optical pathway for transmitting said reference signal through passage defined by a predetermined distance approximately equal to said sample passage;

a probe for containing said sample and reference optical pathways, said probe having a passage for providing sample to the sample passage, said reference optical pathway being situated in said probe adjacent said sample optical pathway and sealed from sample ingress;

nozzle means constructed to receive said probe in a sample process line, said nozzle means having sealing means to prevent sample escape, said sealing means being constructed to allow said probe of the fluid opacity sensor to be withdrawn from the sample process line for cleaning the sample passage and setting offset adjustment;

a photodetector for each optical pathway for receiving said sample signal and said reference signal being propagated along said sample optical pathway and said reference optical pathway, each of said photodetectors being situated inside said probe, both of said optical pathways being defined by optical fiber means spaced apart from and axially aligned with said photodetectors at the predetermined distance of the sample and reference passage, said reference optical pathway being exposed to a similar environment as said sample optical pathway; and means for measuring variations in light intensity of said sample and reference signals for determining opacity.

2. A fluid opacity sensor, as recited in claim 1, wherein said measuring means includes signal processing means for measuring log ratios.

3. A fluid opacity sensor, as recited in claim 1, wherein said dividing means includes a coupler connected to two optical fibers for transmitting the sample signal and the reference signal.

4. A fluid opacity sensor, as recited in claim 1, further comprising computer means for displaying the measured opacity.

5. A fiber optic fluid opacity sensor as recited in claim 1, wherein said probe comprises a body with threaded ends.

6. A fiber optic fluid opacity sensor as recited in claim 5, further comprising a container for holding said means for measuring variations in light intensity, said container having a threaded portion for receiving one of the threaded ends of said probe.

7. A fiber optic fluid opacity sensor as recited in claim 6, further comprising a cap for receiving the other threaded end of said probe.

8. A fiber optic fluid opacity sensor as recited in claim 1, wherein said passage in said probe includes a flared sample pathway outboard.

9. A fiber optic fluid opacity sensor as recited in claim 2, wherein said signal processing means is calibrated over a range of six units referenced to air.

10. A fiber optic fluid opacity sensor, as recited in claim 8, wherein the distance of said sample passage is about 1.6 mm.

11. A fiber optic fluid opacity sensor for measuring opacity of a sample in a sample process line, comprising:
  a light source;
  means for dividing light from said light source into a sample signal and a reference signal;
  a sample optical pathway for transmitting said sample signal through a sample in a passage defined by a predetermined distance;
  a reference optical pathway for transmitting said reference signal through a reference passage with a distance approximately equal to the predetermined distance of the sample passage;
  a photodetector for each optical pathway for receiving said sample signal and said reference signal being propagated along said sample and reference optical pathways, each of said optical pathways being defined by an optical fiber spaced apart from and axially aligned with said photodetectors at the predetermined distance, said reference optical pathway being sealed from sample ingress at a location substantially adjacent said sample optical pathway and being exposed to a similar environment;
  a probe for positioning said sample and reference optical pathways in a sample, said probe providing sample access for the sample passage and sealing the reference passage from sample ingress, each of said photodetectors being situated inside said probe;
  nozzle means in the sample process line constructed to receive said probe, said nozzle means having sealing means for sealing said probe in the sample process line, said sealing means being constructed to allow said probe to be partially withdrawn for cleaning the sample passage and maintenance; and
  signal processing means for measuring variations in light intensity of said sample and reference signals for determining opacity with log ratios of the signals.

12. A fiber optic fluid opacity sensor, as recited in claim 11, further comprising computer means for further processing said signals for determining opacity.

13. A fiber optic fluid opacity sensor as recited in claim 11, wherein said probe comprises a body with threaded ends.

14. A fiber optic fluid opacity sensor as recited in claim 13, further comprising a container for holding said signal processing means, said container having a threaded portion for receiving one of the threaded ends of said probe.

15. A fiber optic fluid opacity sensor as recited in claim 14, further comprising a cap for receiving the other threaded end of said probe.

16. A fiber optic fluid opacity sensor as recited in claim 11, wherein said sample passage includes a flared sample pathway outboard.

17. A fiber optic fluid opacity sensor as recited in claim 11, wherein said signal processing means is calibrated over a range of six units referenced to air.

18. A fiber optic fluid opacity sensor, as recited in claim 16, wherein the distance of said sample passage is about 1.6 mm.

* * * * *